United States Patent [19]

King et al.

[11] Patent Number: 4,481,286

[45] Date of Patent: Nov. 6, 1984

[54] LIGANDS AND PHOTOGRAPHIC PROCESS

[75] Inventors: Patrick F. King, Needham; Stephen G. Stroud, Brighton, both of Mass.

[73] Assignee: Polaroid Corporation, Cambridge, Mass.

[21] Appl. No.: 437,611

[22] Filed: Oct. 29, 1982

[51] Int. Cl.³ .......................... G03C 5/54; G03C 1/42
[52] U.S. Cl. ..................................... 430/441; 430/218; 430/225; 430/442; 430/484; 430/485
[58] Field of Search ............... 430/224, 225, 243, 441, 430/442, 484, 485, 218

[56] References Cited

U.S. PATENT DOCUMENTS

| | | | |
|---|---|---|---|
| 3,255,001 | 6/1966 | Blout et al. | 430/225 |
| 3,563,739 | 2/1971 | Idelson | 430/224 |
| 3,629,336 | 12/1971 | Idelson | 260/590 |
| 3,705,184 | 12/1972 | Goulston et al. | 430/243 |
| 3,789,062 | 1/1974 | Idelson | 260/463 |

Primary Examiner—Richard L. Schilling
Attorney, Agent, or Firm—Gaetano D. Maccarone

[57] ABSTRACT

Novel compounds which are capable of forming a coordination complex with a metal and which include a silver halide developing substituent or a precursor thereof. The compounds are useful as silver halide developing agents and as intermediates for dye developers which are utilized in photographic applications.

5 Claims, No Drawings

LIGANDS AND PHOTOGRAPHIC PROCESS

BACKGROUND OF THE INVENTION

This application is directed to novel compounds and, more particularly, to compounds which are useful in photography and as intermediates in the preparation of metallized dye developers which are useful in photographic applications.

Compounds which are coordinating agents and which can form a coordination complex with a metal are known in the art. Those atoms of such compounds which are linked directly to the metal cation are called coordinating, or donor, atoms and each metal ion requires several of these atoms to make up its coordination number. According to the number of coordinating atoms which it contains the complex forming agent, or ligand, is said to be uni-dentate, bi-dentate and so forth. Coordinating agents are further classified as organic or inorganic. In organic agents the coordination atoms, generally O, N or S, are attached to the carbon skeleton of an organic molecule. Particularly useful applications of such compounds lie in the dye field to form stable metal-dye complexes, commonly referred to as metallized dyes, and in photography to prepare stable metal-dye developer complexes, commonly referred to as metallized dye developers.

SUMMARY OF THE INVENTION

It is the object of this invention to provide novel compounds which are substantially colorless organic coordinating agents.

It is another object to provide such compounds which include a silver halide developing substituent or a precursor thereof.

It is a further object to provide such compounds which are useful in the preparation of metallized dye developers.

It is still another object to provide compounds which are useful as auxiliary developers in conjunction with other silver halide developing agents.

A further object is to provide photographic products and processes which utilize the compounds.

BRIEF SUMMARY OF THE INVENTION

These and other objects and advantages are accomplished in accordance with the invention by providing novel ligands which are capable of forming a coordination complex with a metal and which include at least one silver halide developing substituent or a precursor thereof. The compounds are represented by the formula

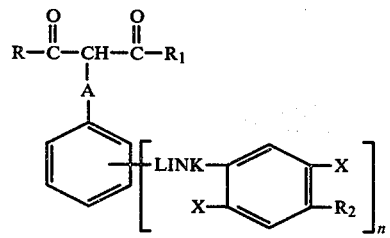

FORMULA A wherein R and $R_1$ may be the same or different and can be hydrogen, alkyl, preferably having from 1 to 6 carbon atoms, alkoxyalkyl, preferably having from 1 to 6 carbon atoms, alkylamino, preferably having from 1 to 6 carbon atoms, aryl, e.g., phenyl or a phenylamino, or a substituted derivative of such radicals; A is alkylene having from 0 to 6 carbon atoms, preferably methylene; LINK is any suitable divalent linking moiety such as alkylene, ether such as —O—$CH_2$—, sulfonamide such as —$SO_2$—NH— or —NH—$SO_2$—, carboxamide such as CONH— or —NHCO—, and the like; X is —OH or a substituent capable of being converted to —OH such as —$OCH_3$ or

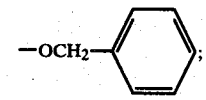

$R_2$ is H, alkyl, preferably having from 1 to 6 carbon atoms, aryl such as phenyl or aryl substituted with alkyl such as phenyl substituted with methyl; and n is 1 or 2.

A preferred sub-generic group of compounds according to the invention is represented by the formula

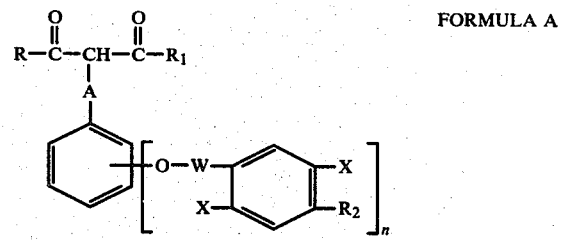

FORMULA A wherein W is alkylene having from 1 to 6 carbon atoms, preferably propylene. Compounds within Formula B have been shown to perform very well as auxiliary developer agents. In photographic testing these compounds have exhibited short induction times and low stain, or post-processing transfer.

DESCRIPTION OF THE PREFERRED EMBODIMENTS

Preferred ligands according to the invention are represented by the formulas

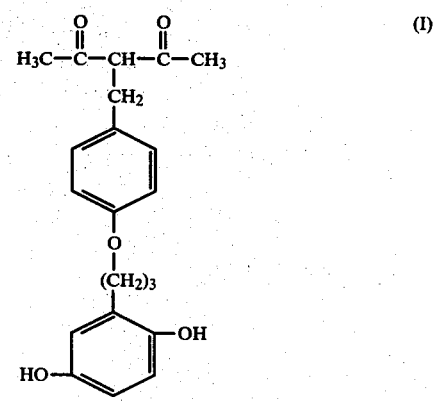

(I)

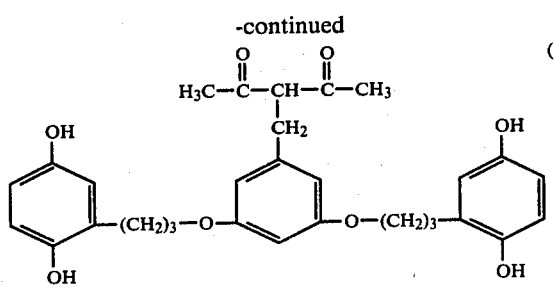

(II)

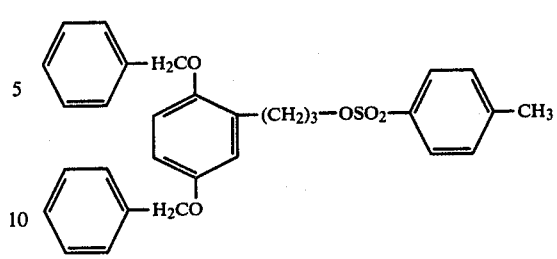

(IV)

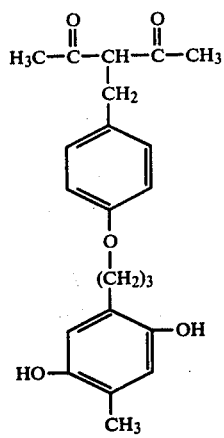

(III)

The preparation of the novel ligands of the invention can be carried out by reactions which are known in the art and such techniques will be apparent from the disclosure which follows.

As mentioned previously, the compounds of the invention are useful as silver halide developing agents, both individually or as auxiliary developing agents in conjunction with other silver halide developers, and also as intermediates in the preparation of dye developers such as are disclosed and claimed in applicants' copending patent application Ser. No. 437,617, filed on even date herewith. In a preferred embodiment R and $R_1$ are the same and the ligands are symmetrical. It has been found that when such symmetrical ligands according to the invention chelate to a metallized dye moiety the resulting metallized dye developer advantageously has only one isomeric form. This is beneficial to the use of these dye developers in photographic applications since it has been shown that when a dye developer has more than one isomeric form the respective isomers can have different physical and photographic properties with resultant photographic complications.

The invention will now be further described in detail with respect to specific preferred embodiments by way of examples, it being understood that these are intended to be illustrative only and the invention is not limited to the materials, conditions, process parameters, etc. recited therein.

EXAMPLE I

A mixture of a blocked developer tosylate compound (100 g; 0.2 mole) represented by the formula p-hydroxybenzaldehyde (25 g, 0.2 mole) and potassium carbonate (41.4 g, 0.3 mole) in acetone (400 ml) and dimethylformamide (400 ml) was heated on a steam cone for 12 hours. The cooled solution was diluted with two liters of ethyl ether, filtered, washed well with three 500 ml volumes of water, then with salt solution and dried over calcium sulfate. The resulting crude solid was purified by high performance liquid chromatography to give 61 g of a white solid represented by the formula

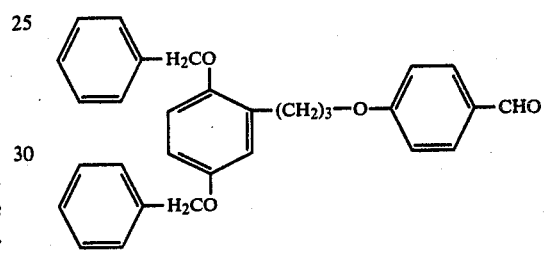

(V)

$C_{30}H_{28}O_4$ requires 79.65% C and 6.19% H. Elemental analysis found 79.64% C and 6.43% H.

A mixture of Compound V (46 g, 0.1 mole), acetylacetone (10.2 g, 0.1 mole), piperidine (0.25 g, 0.003 mole), and hexanoic acid (0.7 g, 0.006 mole) in benzene (300 ml) was refluxed for 12 hours with azeotropic removal of the water. The cooled solution was diluted with 300 ml of ethyl ether and washed consecutively with cold 10% hydrochloric acid, water, 5% sodium bicarbonate solution and salt solution followed by drying over sodium sulfate. Solvent removal yielded a crude oil which was purified by HPLC to give 27 g of a clear oil represented by the formula

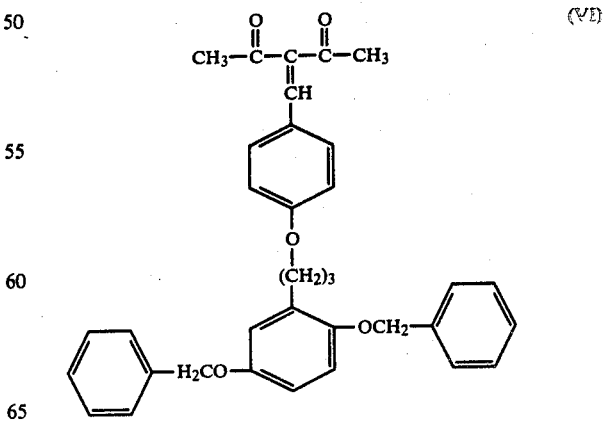

(VI)

A solution of Compound VI (20 g, 0.037 mole) in 75 ml of tetrahydrofuran and 50 ml of absolute ethanol was purged with argon for 20 minutes in a hydrogenation vessel. A 10% Pd/C catalyst was added to the solution in a paper envelope and the slurry was reduced under hydrogen on a Paar apparatus. The solution was filtered through a diatomaceous earth pad and the solvent removed under vacuum once the theoretical amount of hydrogen had been taken up. The resultant oil crystallized on standing to give 12 g (90% yield) of a white solid, Compound I.

$C_{21}H_{24}O_5$ requires 70.8% C and 6.7% H. Elemental analysis found 71.21% C and 71.1% H.

compound IV. The mixture was stirred and heated at 105° C. for 3 hours.

The cooled reaction mixture was poured slowly into 2.5 liters of water with stirring and the mixture acidified to pH 1 with concentrated hydrochloric acid causing a dark oil to form. The mixture was stirred overnight during which time the crude oil solidified. The solid was collected, washed with water and recrystallized from 4 liters of 2-propanol to yield 79 g of an off-white solid represented by the formula

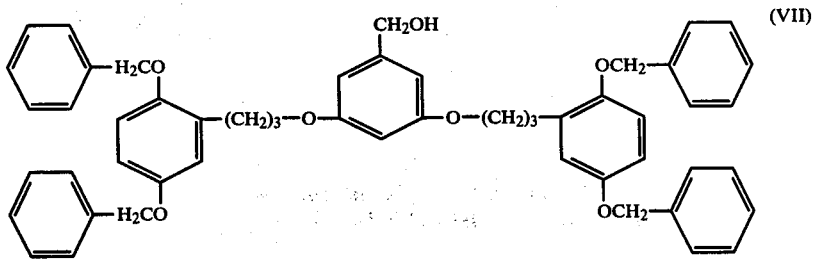

EXAMPLE II

To a solution of 3,5-dihydroxybenzoic acid (150 g, 0.94 mole) in 2 liters of tetrahydrofuran in a 5 liter, 3 necked round bottom flask there were added under a nitrogen atmosphere, dropwise over a ¾ hour period, 190 ml (2.0 mole) of $BH_3.S(CH_3)_2$. The addition was exothermic and a white precipitate formed. The mixture was stirred for 30 minutes and refluxed for 30 hours.

To the cooled reaction mixture there was added carefully one liter of methanol with stirring. Excess solvent was removed under vacuum leaving a dark oil/solid.

The filtrate was refrigerated to yield an additional 26 g of product.

A solution of compound VII (103 g, 0.13 mole) and pyridinium dichromate (75 g, 0.20 mole) in 750 ml of methylene chloride in a 2 liter round bottom flask was stirred under nitrogen atmosphere for 18 hours. The reaction mixture was filtered through a diatomaceous earth plug and then through a silica column to remove any microinsolubles. The filtrate was chromatographed by HPLC to yield a yellow oil which solidified upon standing overnight. The solid was recrystallized from 2-propanol to give 96.3 g of a slightly yellow solid represented by the formula

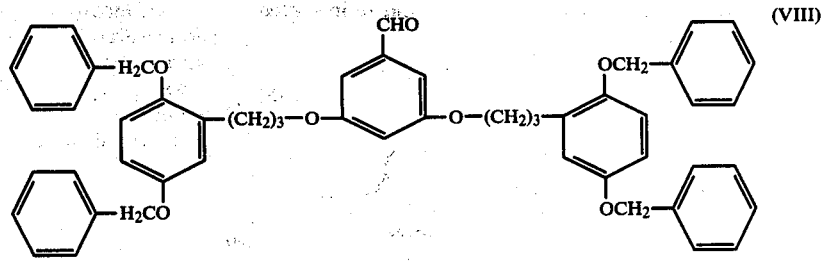

Water (300 ml) was added to the crude solid and the mixture stirred for 30 minutes. The product was collected, washed with 250 ml of cold water and dried under vacuum to give 81.4 g of a white granular solid, 3,5-dihydroxybenzyl alcohol, m.p. 181°–184° C. The filtrate was refrigerated to yield an additional 13.9 g of the product. The structure of the product was confirmed by a $^1H$ NMR spectrum.

To a solution of 3,5-dihydroxybenzyl alcohol (25.0 g, 0.18 mole) in 700 ml of dimethylformamide in a 2 liter round bottom flask there was added slowly, under nitrogen and with stirring, a 57% oil dispersion of NaH (16.0 g, 0.38 mole). The mixture was stirred for 30 minutes and to it there were added 182 g (0.36 mole) of $C_{53}H_{50}O_7$ requires 79.67% C, 6.31% H and 14.02% O. Elemental analysis found 79.65% C, 6.35% H and 13.95% O.

A mixture of compound VIII (96 g, 0.12 mole), acetylacetone (12.1 g, 0.12 mole), benzene (1.5 liters), piperidine (1 ml) and hexanoic acid (2 ml) in a 2 liter round bottom flask was refluxed overnight and then cooled to room temperature. The solvents were removed by rotary evaporation leaving a sticky yellow oil. The crude oil was triturated repeatedly with boiling 2-propanol (5 liters total). Upon cooling a fluffy yellow solid precipitated from the propanol extractions. The solid was collected, washed with 2-propanol and dried under vacuum to give 76.3 g of a light yellow solid represented by the formula

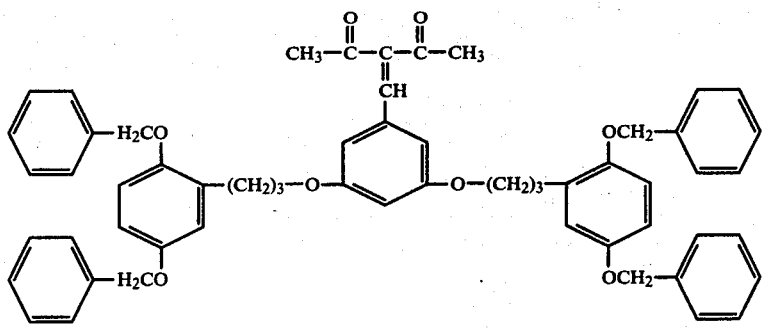

(IX)

$C_{58}H_{56}O_8$ requires 79.06% C, 6.41% H and 14.53% O. Elemental analysis found 79.08% C, 6.58% H and 14.69% O.

A solution of compound IX (30 g, 0.034 mole) in 100 ml of ethanol and 150 ml of tetrahydrofuran was formed in a hydrogenation vessel and 10% Pd/C (4 g) catalyst was added to it. The mixture was hydrogenated and hydrogen uptake ceased after approximately 24 hours (total hydrogen uptake was slightly in excess of theoretical). The mixture was filtered through a diatomaceous earth plug to remove catalyst and the filtrate was poured into 1.5 liters of water with stirring. The product was extracted 5 times with 200 ml of diethyl ether. The ether extracts were dried over sodium sulfate, filtered and the ether evaporated to leave an oil which was dried on vacuum to yield 11.5 g of a brown solid compound II which oiled when exposed to atmospheric moisture.

EXAMPLE III

A mixture of 4-hydroxybenzaldehyde (13.8 g, 0.113 mole), 57.5 g (0.111 mole) of a compound represented by the formula

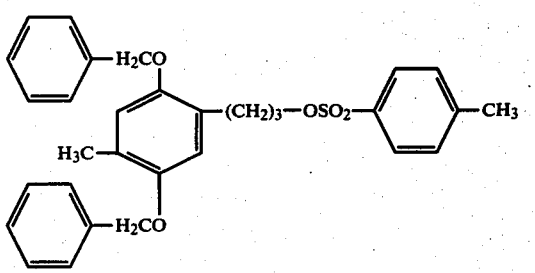

(X)

potassium carbonate (23 g, 0.167 mole), acetone (225 ml) and dimethylformamide (225 ml) was refluxed under nitrogen for 6 hours. The cooled mixture was allowed to stir overnight. Ethyl ether (1 liter) was added to the reaction mixture with stirring and the mixture was filtered. The filtrate was washed with 300 ml of 10% hydrochloric acid and twice with 300 ml of saturated sodium sulfate solution and dried over sodium sulfate. The solvent was removed by evaporation leaving a yellow oil which quickly solidified to an off-white solid. The crude product was recrystallized from 250 ml of 2-propanol to give 42.8 g of a white solid represented by the formula

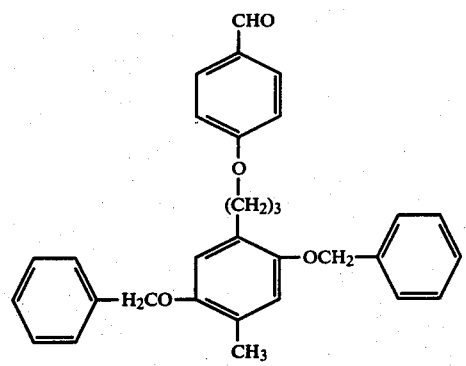

(XI)

$C_{31}H_{30}O_4$ requires 79.80% C, 6.48% H and 13.72% O. Elemental analysis found 79.88% C, 6.53% H and 13.40% O.

A mixture of compound XI (42.5 g, 0.091 mole), acetylacetone (10 g, 0.1 mole), benzene (1 liter), piperidine (0.7 ml) and hexanoic acid (1.5 ml) was refluxed for 24 hours with removal of water. The solvent and excess volatiles were removed from the mixture under vacuum leaving a crude red oil to which there were added 150 ml of 2-propanol. The mixture was stirred with occasional scratching and the product slowly solidified. The slurry was stirred overnight and the product was collected, washed with 100 ml of 2-propanol and dried under vacuum to give 41.5 g of a light yellow solid represented by the formula

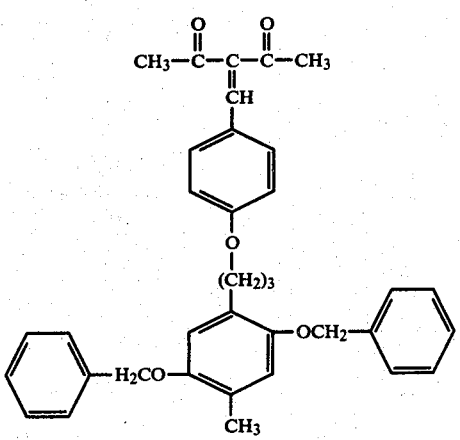

(XII)

$C_{36}H_{36}O_5$ requires 78.80% C, 6.61% H and 14.58% O. Elemental analysis found 79.04% C, 6.74% H and 14.08% O.

A solution of compound XII (5.8 g, 0.011 mole) in 150 ml of ethanol and 75 ml of tetrahydrofuran was formed and nitrogen bubbled through it to degas it. A catalyst, 10% Pd/C, was added and the mixture was hydrogenated for 18 hours after which the hydrogen uptake ceased. The catalyst was removed by filtration through a diatomaceous earth plug and the solvent removed under vacuum to give a brown oil which slowly solidified. The crude solid was stirred with 50 ml of 2-propanol until it was finely dispersed, then collected, washed with 2-propanol and dried under vacuum to give 2.5 g of a light pink solid, compound III.

$C_{22}H_{26}O_5$ requires 71.33% C, 7.08% H and 21.6% O. Elemental analysis found 71.53% C, 7.02% H, and 21.15% O.

EXAMPLE IV

As a control a film unit was prepared as follows: the photosensitive element was made up of a transparent subcoated polyethylene terephthalate photographic film base on which the following layers were coated in succession:

1. a layer comprising about 3000 mgs/m$^2$ of gelatin and about 60 mgs/m$^2$ of muccochloric acid;
2. a silver iodobromide emulsion layer comprising about 1050 mgs/m$^2$ of silver; about 800 mgs/m$^2$ of gelatin and about 100 mgs/m$^2$ of 4'-methylphenyl hydroquinone; and
3. a top coat layer comprising about 500 mgs/m$^2$ of gelatin and about 5 mgs/m$^2$ of succindialdehyde.

The image receiving element comprised a transparent subcoated polyethlene terephthalate photographic film base upon which there were coated the following layers in succession:

1. as a polymeric acid layer approximately 9 parts of a ½ butyl ester of polyethylene/maleic anhydride copolymer and 1 part of polyvinyl butyral at a coverage of about 26,460 mgs/m$^2$.
2. a timing layer coated at a coverage of about 2422 mgs/m$^2$ comprising 90% of a 60/29/6/4/0.4 pentapolymer of butylacrylate, diacetone acrylamide, methacrylic acid, styrene and acrylic acid and 10% of polyvinyl alcohol as a permeator.
3. an image receiving layer coated at a coverage of about 3122 mgs/m$^2$ of a graft copolymer comprised of 4-vinylpyridine (4VP) and vinyl benzyl trimethyl ammonium chlorid (TMQ) grafted onto hydroxyethyl cellulose (HEC) at a ratio HEC/4VP/TMQ of 2.2/2.2/1; and about 108 mgs/m$^2$ of 1,2-butanediol diglycidyl ether; and
4. an overcoat layer of about 430 mgs/m$^2$ of polyvinylalcohol.

The film unit was processed with a processing composition made up as follows:

|  | Weight Percent |
|---|---|
| Water | 41.4 |
| Titanium dioxide | 48.5 |
| Oximated polydiacetone acrylamide | 0.672 |
| Potassium hydroxide | 4.60 |
| Benzotriazole | 0.462 |
| 6-methyl uracil | 0.252 |
| Colloidal silica | 0.233 |
| N—phenethyl-α-picolinium bromide | 1.07 |
| 3,5-dimethylpyrazole | 0.167 |
| 1-(4-hydroxyphenyl)-tetrazoline-5-thione | 0.041 |
| N—hydroxyethyl-N,N'N'-triscarboxymethyl ethylene diamine | 0.629 |
| Bis(2-aminoethyl)sulfide | 0.065 |
| 4-aminopyrazole(3,4d)pyrimidine | 0.210 |
| Allopurinol | 0.069 |
| HOOC—[indole]—[indole]—NH—SO$_2$—C$_{16}$H$_{33}$ structure | 0.294 |
| C$_{18}$H$_{37}$O—[naphthol-COOH]—[naphthol-COOH] structure | 1.31 |

The photosensitive element was processed in the dark, without being exposed, at room temperature by passing it in superposed relationship with the image receiving element through a pair of rollers at a gap spacing of 0.0030 inch. The rate and amount of developed silver were measured as a function of infrared absorption.

Another sample of the same photosensitive element was exposed (0.5 meter-candle-second) with white light through the transparent base and processed as described above.

A film unit according to the invention (FILM UNIT A) was prepared. Film Unit A was the same as the control with the exception that layer 2 of the photosensitive element contained about 185 mgs/m$^2$ of compound III, an equimolar amount, in place of the 4'-methylphenyl hydroquinone. Samples of this film unit were processed, with and without exposure, as described above.

|  |  | Induction Time (Seconds) | Maximum Density |
|---|---|---|---|
| CONTROL | Not Exposed | 8.5 | 1.01 |
|  | Exposed | 0.7 | 1.67 |
| FILM UNIT A | Not Exposed | 20.3 | 0.96 |
|  | Exposed | 0.2 | 1.68 |

The data show that compound III is useful as a silver halide developing agent since it discriminates between fog development (no exposure) and exposure development. The data also show that compound III of the invention develops exposed silver more rapidly than 4'methyl phenyl hydroquinone while exhibiting a much longer induction time for fog development.

The control and Film Unit A were also subjected to a D$_{min}$ stain test. The film units were processed at room temperature (75° F., 45% R.H.), initially and after five days, and after being in an oven at 120° F. and 75% R.H. for five days. The film units were processed as described above with the exception that a different processing composition was used. The processing composition did not include any opacifying dyes and was made as follows:

| | Weight Percent |
|---|---|
| Water | 43.1 |
| Titanium dioxide | 49.4 |
| Oximated polydiacetone acrylamide | 0.680 |
| Potassium hydroxide | 4.34 |
| Benzotriazole | 0.471 |
| 6-methyl uracil | 0.428 |
| Colloidal silica | 0.237 |
| N—phenethyl-α-picolinium bromide | 1.09 |
| 3,5-dimethylpyrazole | 0.171 |
| N—hydroxyethyl-N,N'N'—triscarboxymethyl ethylene diamine | 0.642 |
| Bis(2-aminoethyl)sulfide | 0.017 |
| 4-aminopyrazolo(3,4d)pyrimidine | 0.214 |

| | | START | | | Δ 5 DAYS | |
|---|---|---|---|---|---|---|
| | | R | G | B | R | G | B |
| CON- | R.T. | 0.30 | 0.31 | 0.32 | +0.04 | +0.09 | +0.16 |
| TROL | 120°/75% | 0.30 | 0.31 | 0.32 | +0.08 | +0.21 | +0.41 |
| A | R.T. | 0.27 | 0.29 | 0.29 | +0.02 | +0.03 | +0.06 |
| | 120°/75% | 0.27 | 0.29 | 0.29 | +0.04 | +0.11 | +0.26 |

It is apparent that Film Unit A which includes compound III of the invention exhibited substantially reduced stain levels, or $D_{min}$ increase, in comparison to the Control.

EXAMPLE V

As a control a film unit was prepared as follows: the photosensitive element was made up of a transparent subcoated polyethylene terephthalate photographic film base on which there were coated in succession the following layers:

1. a layer comprising about 3000 mgs/m² of gelatin and about 60 mgs/m² of muccochloric acid;

2. a yellow dye developer layer comprising about 820 mgs/m² of a yellow dye developer represented by the formula

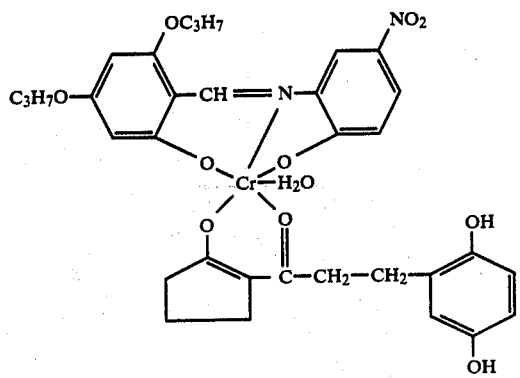

and about 328 mgs/m² of gelatin;

3. a blue sensitive silver iodobromide emulsion layer comprising about 1050 mgs/m² of silver, about 800 mgs/m² of gelatin and about 100 mgs/m² of 4'-methyl phenyl hydroquinone; and 4. a top coat layer comprising about 500 mgs/m² of gelatin and about 5 mgs/m² of succindialdehyde.

The image receiving element and the processing composition (with opacifying dyes) were the same as those described in Example IV.

The negative was exposed (0.5 meter-candle-second) through the transparent base on a sensitometer to a test exposure scale with white light and processed by passing it, in superposed relationship with the image receiving element, through a pair of rollers at a gap spacing of about 0.0030 inch.

Three film units according to the invention (Film Units B-D) were prepared. These were the same as the Control with the exception that the silver iodobromide emulsion layer contained 95 mgs/m², 185 mgs/m² and 370 mgs/m² of compound III respectively (0.5, 1.0 and 2.0 molar amounts, respectively) in place of 4'-methyl phenyl hydroquinone.

The neutral density columns of the images were read on a densitometer to obtain the blue $D_{max}$ and $D_{min}$ values. In addition, the speed of the blue curve (defined as the negative log of the relative exposure required to give blue absorption in the neutral column a reflection density of 0.75) was measured.

| FILM UNIT | BLUE $D_{MAX}$ | BLUE $D_{MIN}$ | BLUE SPEED |
|---|---|---|---|
| CONTROL | 2.19 | 0.27 | 2.15 |
| B | 2.37 | 0.31 | 1.74 |
| C | 2.27 | 0.31 | 1.97 |
| D | 2.34 | 0.30 | 1.93 |

EXAMPLE VI

As a control a film unit was prepared as follows: the photosensitive element was made up of a transparent subcoated polyethylene terephthalate film base on which there were coated the following layers in succession:

1. a carrier layer coated at a coverage of about 3000 mgs/m² and comprising about 100 parts of a 60/29/6/4/0.4 penta-polymer of butrylacrylate, diacetone acrylamide, methacrylic acid, styrene and acrylic acid and 1.5 parts of gelatin;

2. a cyan dye developer layer comprising about 511 mgs/m² of a cyan dye developer represented by the formula

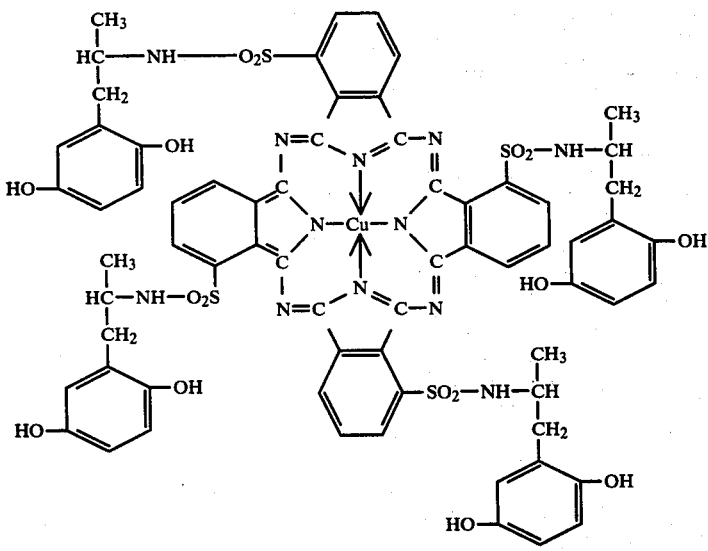

about 70 mgs/m² of 4'-methylphenyl hydroquinone and about 255 mgs/m² of gelatin;

3. a red sensitive silver iodobromide emulsion layer comprising about 1378 mgs/m² of silver and about 820 mgs/m² of gelatin;

4. an interlayer comprising about 2200 mgs/m² of a mixture of 95 parts of the pentapolymer described in layer 2 and 5 parts of polyacrylamide, and 44 mgs/m² of succindialdehyde;

5. a magenta dye developer layer comprising about 449 mgs/m² of a magenta dye developer represented by the formula 10. a blue sensitive silver iodobromide emulsion layer comprising about 535 mgs/m² of silver, about 500 mgs/m² of gelatin and about 135 mgs/m² of 4'-methyl phenyl hydroquinone; and 11. a top coat layer of about 400 mgs/m² of gelatin.

The image receiving element was the same as that described in Example IV.

The film unit was processed with a processing composition made up as follows:

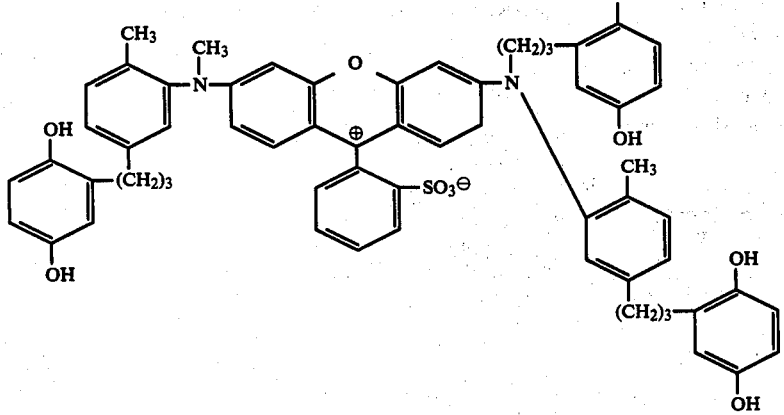

about 171 mgs/m² of 2-phenylbenzimidazole and about 225 mgs/m² of gelatin;

6. a green sensitive silver iodobromide emulsion layer comprising about 677 mgs/m² of silver and about 495 mgs/m2 of gelatin;

7. an interlayer comprising about 1188 mgs/m² of the 95/5 pentapolymer/polyacrylamide mixture described in layer 5;

8. a gelatin layer coated at a coverage of about 100 mgs/m²;

9. a yellow dye developer layer comprising about 689 mgs/m² of the yellow dye developer illustrated in Example V and about 276 mgs/m² of gelatin;

|  | Weight Percent |
|---|---|
| Water | 40.9 |
| Titanium dioxide | 47.9 |
| Oximated polydiacetone acrylamide | 0.660 |
| Potassium hydroxide | 4.36 |
| Benzotriazole | 0.456 |
| 6-methyl uracil | 0.249 |
| Hypoxanthine | 0.101 |
| 6-bromo-5-methyl-4-azabenzimidazole | 0.101 |
| Colloidal silica | 0.230 |
| N—phenethyl-α-picolinium bromide | 1.06 |
| Polyethylene glycol (MW 4000) | 0.373 |
| 3,5-dimethylpyrazole | 0.166 |
| 2-methylimidazole | 0.690 |
| 1-(4-hydroxyphenyl)-tetrazoline-5-thione | 0.039 |
| N—hydroxyethyl-N,N'N'-triscarboxymethyl ethylene | 0.622 |

| | Weight Percent |
|---|---|
| diamine | |
| Nickel acetate | 0.414 |
| HOOC-...-NH—SO₂—C₁₆H₃₃ (structure) | .290 |
| C₁₈H₃₇O-...-COOH HOOC-...-OH (structure) | 1.38 |

The photosensitive element was exposed with white light (2.0 meter-candle-seconds) through the transparent base to a test exposure scale and processed by passing it, in superposed relationship with the image receiving element, through a pair of rollers at a gap spacing of 0.0030 inch.

An additional film unit according to the invention was prepared (Film Unit E) which was the same as the Control with the exception that layer 10 of the photosensitive element contained 250 mgs/m² of compound III (an equimolar amount) in place of 4'-methyl phenyl hydroquinone.

| FILM UNIT | $D_{max}$ | | | $D_{min}$ | | | Speed | | |
|---|---|---|---|---|---|---|---|---|---|
| | R | G | B | R | G | B | R | G | B |
| CONTROL | 1.50 | 1.81 | 1.81 | 0.19 | 0.19 | 0.20 | 1.81 | 1.76 | 1.57 |
| E | 1.46 | 1.79 | 1.79 | 0.18 | 0.20 | 0.22 | 1.83 | 1.72 | 1.61 |

The image obtained from Film Unit E exhibited more saturation in the color columns and improved inter-image effects.

Although the invention has been described in detail with respect to various embodiments thereof, these are intended to be illustrative only and not limiting of the invention but rather those skilled in the art will recognize that modifications and variations may be made therein which are within the spirit of the invention and the scope of the appended claims.

What is claimed is:

1. A photographic method which comprises treating an exposed silver halide emulsion with an aqueous alkaline processing composition containing a silver halide developing agent which is represented by the formula

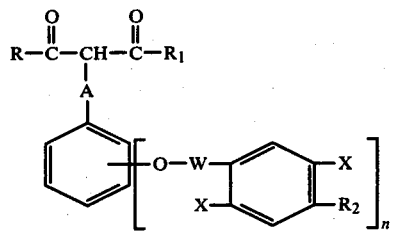

wherein W is alkylene having from 1 to 6 carbon atoms, R and R₁ are the same or different and are selected from the group consisting of H, alkyl, alkoxyalkyl, alkylamino and aryl; A is alkylene having from 1 to 6 carbon atoms; X is —OH or a substituent capable of being converted to —OH; R₂ is H, alkyl or aryl; and n is 1 or 2.

2. A photographic method as defined in claim 1 wherein W is propylene.

3. A photographic method as defined in claim 2 wherein R and R₁ are the same and are each alkyl having from 1 to 6 carbon atoms.

4. A photographic method as defined in claim 3 wherein A is methylene.

5. A photographic method as defined in claim 4 wherein R₂ is H, alkyl having from 1 to 6 carbon atoms or phenyl.

* * * * *